(12) United States Patent
Force Aldred et al.

(10) Patent No.: US 12,202,898 B2
(45) Date of Patent: *Jan. 21, 2025

(54) HEAVY CHAIN ANTIBODIES BINDING TO CD19

(71) Applicant: TeneoTwo, Inc., Newark, CA (US)

(72) Inventors: Shelley Force Aldred, Newark, CA (US); Wim van Schooten, Newark, CA (US); Katherine Harris, Newark, CA (US); Udaya Rangaswamy, Newark, CA (US); Nathan Trinklein, Newark, CA (US)

(73) Assignee: TeneoTwo, Inc., Newark, CA (US)

( * ) Notice: Subject to any disclaimer, the term of this patent is extended or adjusted under 35 U.S.C. 154(b) by 1020 days.

This patent is subject to a terminal disclaimer.

(21) Appl. No.: 17/260,213

(22) PCT Filed: Jul. 19, 2019

(86) PCT No.: PCT/US2019/042633
§ 371 (c)(1),
(2) Date: Jan. 13, 2021

(87) PCT Pub. No.: WO2020/018922
PCT Pub. Date: Jan. 23, 2020

(65) Prior Publication Data
US 2021/0332133 A1  Oct. 28, 2021

Related U.S. Application Data

(60) Provisional application No. 62/701,281, filed on Jul. 20, 2018.

(51) Int. Cl.
| | | |
|---|---|---|
| *C07K 16/28* | (2006.01) |
| *A61K 39/00* | (2006.01) |
| *A61K 45/06* | (2006.01) |
| *A61P 31/00* | (2006.01) |
| *A61P 35/02* | (2006.01) |

(52) U.S. Cl.
CPC .......... *C07K 16/2809* (2013.01); *A61K 45/06* (2013.01); *A61P 31/00* (2018.01); *A61P 35/02* (2018.01); *A61K 2039/505* (2013.01)

(58) Field of Classification Search
CPC ...... A61K 39/395; A61K 38/07; A61K 47/58; A61K 2039/505; A61K 31/337; A61K 31/351; C07K 16/2803; C07K 16/2887; C07K 2317/92; C07K 2319/035; C07K 2317/569; A61P 35/00
See application file for complete search history.

(56) References Cited

U.S. PATENT DOCUMENTS

| | | |
|---|---|---|
| 4,816,567 A | 3/1989 | Cabilly et al. |
| 5,500,362 A | 3/1996 | Robinson et al. |
| 5,821,337 A | 10/1998 | Carter et al. |
| 7,541,513 B2 | 6/2009 | Bruggemann et al. |
| 8,367,888 B2 | 2/2013 | Bruggemann et al. |
| 8,883,150 B2 | 11/2014 | Craig et al. |
| 9,034,324 B2 | 5/2015 | Kalled et al. |
| 9,365,655 B2 | 6/2016 | Craig et al. |
| 11,186,639 B2 | 11/2021 | Harris et al. |
| 11,390,681 B2 | 7/2022 | Harris et al. |
| 11,421,027 B2 | 8/2022 | Trinklein et al. |
| 11,505,606 B2 | 11/2022 | Trinklein et al. |
| 2001/0024811 A1 | 9/2001 | Khosla et al. |
| 2004/0229310 A1 | 11/2004 | Simmons |
| 2005/0048572 A1 | 3/2005 | Reilly et al. |
| 2006/0008548 A1 | 1/2006 | Tung |
| 2009/0098134 A1 | 4/2009 | Buelow |
| 2010/0122358 A1 | 5/2010 | Bruggemann et al. |
| 2013/0156769 A1 | 6/2013 | Kufer et al. |
| 2015/0376287 A1 | 12/2015 | Vu et al. |
| 2016/0166689 A1 | 6/2016 | Adler et al. |
| 2016/0355591 A1 | 12/2016 | Goldenberg et al. |
| 2018/0230225 A1* | 8/2018 | Fan ........................ C07K 16/30 |
| 2019/0352412 A1 | 11/2019 | Force et al. |
| 2020/0048348 A1 | 2/2020 | Trinklein et al. |
| 2020/0085839 A1 | 3/2020 | Sidransky et al. |
| 2020/0157232 A1 | 5/2020 | Trinklein et al. |
| 2020/0339685 A1 | 10/2020 | Schellenberger et al. |
| 2021/0047402 A1 | 2/2021 | Trinklein et al. |
| 2023/0082151 A1 | 3/2023 | Trinklein et al. |
| 2023/0272075 A1 | 8/2023 | Trinklein et al. |

FOREIGN PATENT DOCUMENTS

| | | |
|---|---|---|
| WO | 1996/027011 | 9/1993 |
| WO | 1996/032478 | 10/1996 |
| WO | 1997/034631 | 9/1997 |
| WO | 2001/024811 | 4/2001 |
| WO | 2001/024812 | 4/2001 |

(Continued)

OTHER PUBLICATIONS

Wang et al., "A systematic approach for analysis and characterization of mispairing in bispecific antibodies with asymmetric architecture," (2018) mAbs 10:8, 1226-1235.

Ridgway et al., "Knobs-into-holes' engineering of antibody CH3 domains for heavy chain heterodimerization," (1996) Protein Eng. 9(7):617-621.

Gupta et al., "Constitutive Inflammatory Cytokine Storm: A Major Threat to Human Health," (2019) Journal of Interferon & Cytokine Research 40(1):19-23.

Crescioli et al., "IgG4 Characteristics and Functions in Cancer Immunity," (2016) Curr Allergy Asthma Rep 16:7.

Labrijn et al., "Therapeutic IgG4 antibodies engage in Fab-arm exchange with endogenous human IgG4 in vivo," (2009) Nature Biotechnology 27:767-71.

Muyldermans, "Single domain camel antibodies: current status," 2001; Journal of Biotechnology 74(4):277-302.

Revets et al., "Nanobodies as Novel Agents for Cancer Therapy," (2005) Expert Opinion Biological Therapy 5(1):111-124.

(Continued)

*Primary Examiner* — Jessica H Roark

(57) ABSTRACT

Anti-CD19 heavy chain antibodies (e.g., UniAbs™) are disclosed, along with methods of making such antibodies, compositions, including pharmaceutical compositions, comprising such antibodies, and their use to treat B cell disorders that are characterized by the expression of CD19.

39 Claims, 10 Drawing Sheets

Specification includes a Sequence Listing.

(56) References Cited

FOREIGN PATENT DOCUMENTS

| WO | 2002/066516 | 8/2002 |
| --- | --- | --- |
| WO | 2006/008548 | 1/2006 |
| WO | 2016/048938 | 3/2016 |
| WO | 2017/223111 | 12/2017 |
| WO | 2018/052503 | 3/2018 |
| WO | 2018/237037 | 12/2018 |
| WO | 2019/006072 | 1/2019 |
| WO | 2020/018922 | 1/2020 |

OTHER PUBLICATIONS

Nuttall et al., "Isolation and Characterization of an IgNAR Variable Domain Specific for the Human Mitochondrial Translocase Receptor Tom70," (2003) Eur. J. Biochem. 270:3543-3554.

Nuttall et al., "Selection and Affinity Maturation of IgNAR Variable Domains Targeting Plasmodium falciparum AMA1," (2004) Proteins; Structure, Function and Bioinformatics 55:187-197.

Dooley et al., "Selection and Characterization of Naturally Occuring Single-domain (IgNAR) Antibody Fragments from Immunized Sharks by Phage Display," (2003) Molecular Immunology 40:25-33.

Jaton et al., "Recovery of Antibody Activity Upon Reoxidation of Completely Reduced Polyalanyl Heavy Chain and its Fd Fragment Derived from Anti-2,4-dinitrophenyl Antibody," (1968) Biochemistry 7(12):4185-4195.

Sitia et al., "Developmental Regulation of IgM Secretion: The Role of the Carbosy-terminal Cysteine," (1990) Cell, 60:781-790.

Van der Linden et al., "Comparison of Physical Chemical Properties of Llama VHH Antibody Fragments and Mouse Monoclonal Antibodies," (1999) Biochimica et Biophysica Acta 1431:37-46.

Frenken et al., "Isolation of Antigen Specific Llama $V_{HH}$ Antibody Fragments and Their High Level Secretion by *Saccharomyces cerevisiae*," (2000) J. Biotechnol. 78:11-21.

Ghahroudi et al., "Selection and Identification of Single Domain Antibody Fragments from Camel Heavy-chain Antibodies," (1997) FEBS Letters 414:521-526.

Nguyen et al., "Heavy-chain only antibodies derived from dromedary are secreted and displayed by mouse B cells," (2003) Immunology; 109(1):93-101.

Bruggemann et al., "Heavy-Chain-Only Antibody Expression and B-Cell Development in the Mouse," (2006) Crit. Rev. Immunol. 26(5):377-90.

Zou et al., "Heavy Chain-Only Antibodies are Spontaneously Produced in Light Chain-Deficient," (2007) J Exp Med 204(13):3271-3283.

Geurts et al., "Knockout Rats via Embryo Microinjection of Zinc-finger Nucleases," (2009) Science 325(5939):433.

Iri-Sofla et al., "Nanobody-based Chimeric Receptor Gene Integration in Jurkat Cells Mediated by PhiC31 Integrase," (2011) Experimental Cell Research 317:2630-2641.

Jamnani et al., "T Cells Expressing VHH-directed Oligoclonal Chimeric HER2 Antigen Receptors: Towards Tumor-directed Oligoclonal T Cell Therapy," (2014) Biochimica et Biophysica Acta 1840:378-386.

Gras et al., "BCMAp: An Integral Membrane Protein in the Golgi Apparatus of Human Mature B Lymphocytes," (1995) International Immunology 7(7):1093-1106.

Tai et al., "Novel Anti-B-Cell Maturation Antigen Antibody-drug Conjugate (GSK2857916) Selectively Induces Killing of Multiple Myeloma," (2014) Blood 123(20): 3128-38.

Ali et al., "T Cells Expressing an Anti-B-Cell Maturation Antigen Chimeric Antigen Receptor Cause Remissions of Multiple Myeloma," (2016) Blood 128(13):1688-700.

Kohler et al., "Continuous cultures of fused cells secreting antibody of predefined specificity," (1975) Nature 256:495-497.

Chothia et al., "Canonical structures for the hypervariable regions of immunoglobulins," (1987) Journal of Molecular Biology 196(4):901-917.

Lefranc et al., "IMGT, the international ImMunoGeneTics database," (1999) Nucleic Acids Research, 27(1):209-212.

Zhao et al., "A germline knowledge based computational approach for determining antibody complementarity determining regions," (2010) Molecular Immunology 47(4):694-700.

Chothia et al., "Conformations of immunoglobulin hypervariable regions," (1989) Nature 342:877-883.

Honegger, "Yet Another numbering scheme for immunoglobulin variable domains: an automatic modeling and analysis tool," (2001) Journal of Molecular Biology 309(3):657-670.

Ofran et al. "Automated identification of complementarity determining regions (CDRs) reveals peculiar characteristics of CDRs and B-cell epitopes," (2008) Journal of Immunology 181(9):6230-6235.

Almagro "Identification of differences in the specificity-determining residues of antibodies that recognize antigens of different size: implications for the rational design of antibody repertoires," (2004) Journal of Molecular Recognition 17(2):132-143.

Padlan et al., "Identification of specificity-determining residues in antibodies," (1995) FASEB Journal 9(1):133-139.

Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.

Lund et al., "Expression and characterization of truncated forms of humanized L243 IgG1," (2000) European Journal of Biochemistry 267(24):7246-7256.

Boesch et al., "Highly parallel characterization of IgG Fc binding interactions," (2014) MAbs 6(4):915-927.

Chen et al., "Fusion protein linkers: Property, design and functionality ," (2013) Advanced Drug Delivery Reviews 65(10): 1357-1369.

Hamers-Casterman et al., "Naturally Occurring Antibodies Devoid of Light Chains," (1993) Letters to Nature 363:446-448.

Desmyter et al., "Antigen Specificity and High Affinity Binding Provided by One Single Loop of a Camel Single-domain Antibody," (2001) Journal of Biological Chemistry 276(28):26285-26290.

Jackson et al., "Driving CAR T-cells Forward," (2016) Nature Reviews Clinical Oncology 13:370-383.

Ravetch et al., "Fc Receptors," (1991) Annual Review of Immunology 9:457-492.

Clynes et al., "Fc Receptors are Required in Passie and Active Immunity to Melanoma," (1998) PNAS (USA) 95(2):652-656.

Gazzano-Santoro et al., "A non-radioactive complement-dependent cytotoxicity assay for anti-CD20 monoclonal antibody," (1996) Journal of Immunological Methods 202(2):163-171.

Concepcion et al., "Label-Free Detection of Biomolecular Interactions Using BioLayer Interferometry for Kinetic Characterization," (2009) Combinatorial Chemistry & High Throughput Screening 12(8):791-800.

Menoret et al., "Characterization of Immunoglobulin Heavy Chain Knockout Rats," (2010) European Journal of Immunology 40:2932-2941.

Cui et al., "Targeted Integration in Rat and Mouse Embryos with Zinc-finger Nucleases," (2011) Nature Biotechnology 29(1):64-67.

Carpenter et al., "B-cell Maturation Antigen Is a Promising Target for Adoptive T-cell Therapy of Multiple Myeloma," (2013) Clinical Cancer Research 19(8):2048-2060.

Tai et al., "APRIL and BCMA promote human multiple myeloma growth and immunosuppression in the bone marrow microenvironment," (2016) Blood 127(25):3225-3236.

Sanz et al., "B Cells as Therapeutic Targets in SLE," (2010) Nature Reviews Rheumatology 6:326-337.

Dai et al., "Chimeric Antigen Receptors Modified T-cells for Cancer Therapy," (2016) J Natl Cancer Inst 108(7):dvj439.

Omniab, "Naturally Optimized Human Antibodies," (Feb. 23, 2016) retrieved from Internet: URL:http://content.stockpr.com/omniab/db/252/746/file/OmniAb.pdf.

Armitage, "A clinical evaluation of the International Lymphoma Study Group classification of non-Hodgkin's lymphoma," (1997) Blood 89(11):3909-3918.

Hanes et al., "New advances in microsphere-based single-dose vaccines," (1997) Advanced Drug Delivery Reviews 28(1):97-119.

(56) References Cited

OTHER PUBLICATIONS

Langer, "New Methods of Drug Delivery," (1990) Science 249(4976):1527-1533.
Banihashemi et al., "Development of Specific Nanobodies (VHH) for CD19 Immuno-targeting of Human B-lymphocytes," (2018) Iranian Journal of Basic Medical Sciences 21(5):455-464.
Malik et al., "A Novel Fully Human Bispecific CD19 x CD3 Antibody that Kills Lymphoma Cells with Minimal Cytokine Secretion," (2018) 132(1):1671.
Naddafi et al., "Anti-CD19 Monoclonal Antibodies: A New Approach to Lymphoma Therapy," (2015) IJMCM 4(3):143-151.
Sadelain et al., "CD19 Car T Cells," (2017) Cell 171:1471.
Miller et al., "Design, Construction, and In Vitro Analyses of Multivalent Antibodies," (2003) Jour. of Immunology 170(9):4854-4861.
Duncan et al., "Localization of the binding site for the human high-affinity Fc receptor on IgG ," (1988) Nature 332:563-564.
Tao et al., "Structural features of human immunoglobulin G that determine isotype-specific differences in complement activation," (1993) Journal of Experimental Medicine 178(2):661-667.
Canfield et al." The Binding Affinity of Human IgG for its High Affinity Fc Receptor Is Determined by Multiple Amino Acids in the CH2 Domain and Is Modulated by the Hinge Region," J. Exp. Med. 173:1483-1491, (1991) J. Exp. Med. 173:1483-1491.
Armour et al., "Recombinant human IgG molecules lacking Fcγ receptor I binding and monocyte triggering activities," (1999) Eur J Immunol. 29(8):2613-2624.
Shields et al., "High Resolution Mapping of the Binding Site on Human IgG1 for FcγRI, FcγRII, FcγRIII, and FcRn and Design of IgG1 Variants with Improved Binding to the FcγR," (2001) J Biol Chem. 276(9):6591-6604.

\* cited by examiner

| SEQ_aa_CDR1 | SEQ_aa_CDR2 | SEQ_aa_CDR3 |
|---|---|---|
| GFTFSNYW (SEQ ID NO: 1) | INQDGSDK (SEQ ID NO: 7) | ASGVYSFDY (SEQ ID NO: 13) |
| GFTFSSFW (SEQ ID NO: 2) | MNQDGSEK (SEQ ID NO: 8) | |
| GFTFSSYW (SEQ ID NO: 3) | INQDGSEK (SEQ ID NO: 9) | |
| GFSFSDFW (SEQ ID NO: 4) | ISQAGSEK (SEQ ID NO: 10) | |
| GFTFSDYW (SEQ ID NO: 5) | IKQDGSEK (SEQ ID NO: 11) | |
| GFTFSDYY (SEQ ID NO: 6) | INKAGSEE (SEQ ID NO: 12) | |

FIG. 1

| Clone ID # | SEQ_aa_FR1_FR4 | SEQ ID NO: |
|---|---|---|
| 341635 | EVQLVESGGGLVQPGGSLRLSCAASGFTFSNYWMSWVRQAPGKGQEWVATINQDGSDKDYVDSVKGRFTISRDNAKKSLYLQMNSLRAEDTAVYYCASGVYSFDYRGQGTLVTVSS | 14 |
| 341662 | EVQLVESGGGLAQPGGSLRLSCAASGFTFSSFWMSWVRQAPGKGLEWVATMNQDGSEKDYVDSVKGRFTISRDNAKNSLYLQMNSLTAEDTAVYYCASGVYSFDYRGQGTLVTVSS | 15 |
| 341691 | EVQLVESGGGMVQPGGSLRLSCAASGFTFSSYWMSWVRQAPGKGLEWVATINQDGSEKDYVDSVKGRFTISRDNAKKSLLLQMNSLRAEDTAVYYCASGVYSFDYRGQGTLVTVSS | 16 |
| 334354 | EVQLVESGGGLVQPGGSLRLSCAASGFSFSDFWMSWVRQAPGKGLEWVATISQAGSEKDYVDSVKGRFTISRDNAKKSLYLQMNSLRAEDTAVYYCASGVYSFDYRGQGTLVTVSS | 17 |
| 341620 | EVQLVESGGGLVKPGGSLRLSCEASGFTFSSYWMSWVRQAPGKGLEWVAHIKQDGSEKYYVDSVKGRFTISRDNAKNSLYLQMNSLRAEDTAVYYCASGVYSFDYRGQGTLVTVSS | 18 |
| 341671 | EVQLVESGGGLVQPGGSLRLSCVASGFTFSDYWMSWVRQAPGKGLEWVANINKAGSEEFYVDSVKGRFTISRDNAKNSLYLQMDSLRVEDTAVYYCASGVYSFDYRGQGTLVTVSS | 19 |
| 341630 | EVQLVESGGGLVQPGGSLTLSCVASGFTFSDYYMSWIRQAPGKGLEWVANIKQDGSEKFYVDSVKGRFTISRDNPKNSLYLQMDSLRVEDTAVYYCASGVYSFDYRGQGTLVTVSS | 20 |
| 341711 | EVQLVESGGGLVQPGGSLRLSCVASGFTFSSYWMSWVRQAPGKGLEWVANIKQDGSEKEYVDSVKGRFTISRDNAKNSLYLQMNSLRAEDTAVYYCASGVYSFDYRGQGTLVTVSS | 21 |

FIG. 2

| Clone ID # | SEQ_aa_CDR1 | SEQ_aa_CDR2 | SEQ_aa_CDR3 |
|---|---|---|---|
| 341635 | GFTFSNYW (SEQ ID NO: 1) | INQDGSDK (SEQ ID NO: 7) | ASGVYSFDY (SEQ ID NO: 13) |
| 341662 | GFTFSSFW (SEQ ID NO: 2) | MNQDGSEK (SEQ ID NO: 8) | ASGVYSFDY (SEQ ID NO: 13) |
| 341691 | GFTFSSYW (SEQ ID NO: 3) | INQDGSEK (SEQ ID NO: 9) | ASGVYSFDY (SEQ ID NO: 13) |
| 334354 | GFSFSDFW (SEQ ID NO: 4) | ISQAGSEK (SEQ ID NO: 10) | ASGVYSFDY (SEQ ID NO: 13) |
| 341620 | GFTFSSYW (SEQ ID NO: 3) | IKQDGSEK (SEQ ID NO: 11) | ASGVYSFDY (SEQ ID NO: 13) |
| 341671 | GFTFSDYW (SEQ ID NO: 5) | INKAGSEE (SEQ ID NO: 12) | ASGVYSFDY (SEQ ID NO: 13) |
| 341630 | GFTFSDYY (SEQ ID NO: 6) | IKQDGSEK (SEQ ID NO: 11) | ASGVYSFDY (SEQ ID NO: 13) |
| 341711 | GFTFSSYW (SEQ ID NO: 3) | IKQDGSEK (SEQ ID NO: 11) | ASGVYSFDY (SEQ ID NO: 13) |

FIG. 3

| Column 1 | Column 2 | Column 3 | Column 4 | Column 5 |
|---|---|---|---|---|
| Clone ID | Raji cell | Ramos cell | CHO huCD19 | CHO_OFFtgt |
| 341635 | 514.8 | 220.7 | 78.4 | 0.9 |
| 341662 | 509.9 | 220.0 | 76.7 | 1.0 |
| 341691 | 524.2 | 214.7 | 75.1 | 1.0 |
| 334354 | 519.4 | 220.6 | 76.5 | 1.1 |
| 341620 | 20.6 | 94.1 | 6.9 | 1.0 |
| 341671 | 14.9 | 86.0 | 6.4 | 1.0 |
| 341630 | 1.0 | 0.9 | 1.0 | 1.0 |
| 341711 | 1.0 | 1.1 | 1.0 | 1.0 |

FIG. 4

Binding constants for TNB-486 determined at 25 degrees C

|  | $k_a$ (M$^{-1}$s$^{-1}$) | $k_d$ (s$^{-1}$) | $K_D$ |
|---|---|---|---|
| 334354 | 1.980(5)e5 | 7.076(7)e-4 | 3.57(1)nM |

HEAVY CHAIN ANTIBODIES BINDING TO CD19

CROSS REFERENCE TO RELATED APPLICATIONS

This application claims priority benefit to U.S Provisional Patent Application No. 62/701,281, filed on Jul. 20, 2018, the disclosure of which is incorporated by reference herein in its entirety.

FIELD OF THE INVENTION

The present invention concerns human heavy chain antibodies (e.g., UniAbs™) binding to CD19. The invention further concerns methods of making such antibodies, compositions, including pharmaceutical compositions, comprising such antibodies, and their use to treat B-cell disorders that are characterized by the expression of CD19.

BACKGROUND OF THE INVENTION

CD19

CD19, also known as B-Lymphocyte Surface Antigen B4 (UniProt P15391), is a cell surface receptor that is expressed on all human B-cells, but is not found on plasma cells. CD19 is a transmembrane protein that recruits cytoplasmic signaling proteins to the membrane and works within the CD19/CD21 complex to decrease the threshold for B cell receptor signaling pathways. CD19 has a relatively large, 240 amino acid, cytoplasmic tail. The extracellular Ig-like domains are divided by a potential disulfide linked non-Ig-like domain and N-linked carbohydrate addition sites. The cytoplasmic tail contains at least nine tyrosine residues near the C-terminus, some of which have been shown to be phosphorylated. Along with CD20 and CD22, the restricted expression of CD19 to the B-cell lineage makes it an attractive target for the therapeutic treatment of B-cell malignancies. Many monoclonal antibodies and antibody drug conjugates specific to CD19 have been described (e.g., Naddafi et al. 2015, PMC4644525). In addition, anti-CD19 chimeric antigen receptor T-cells have been approved to treat leukemia (e.g., Sadelain et al. 2017, PMID: 29245005).

Heavy Chain Antibodies

In a conventional IgG antibody, the association of the heavy chain and light chain is due in part to a hydrophobic interaction between the light chain constant region and the CH1 constant domain of the heavy chain There are additional residues in the heavy chain framework 2 (FR2) and framework 4 (FR4) regions that also contribute to this hydrophobic interaction between the heavy and light chains.

It is known, however, that sera of camelids (sub-order Tylopoda, which includes camels, dromedaries and llamas) contain a major type of antibodies composed solely of paired H-chains (heavy-chain only antibodies, or UniAbs™). The UniAbs™ of Camelidae (*Camelus dromedarius, Camelus bactrianus, Lama glama, Lama guanaco, Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These UniAbs™ lack the first domain of the constant region (CH1), which is present in the genome, but is spliced out during mRNA processing. The absence of the CH1 domain explains the absence of the light chain in the UniAbs™, since this domain is the anchoring place for the constant domain of the light chain Such UniAbs™ naturally evolved to confer antigen-binding specificity and high affinity by three CDRs from conventional antibodies, or fragments thereof (Muyldermans, 2001; *J Biotechnol* 74:277-302; Revets et al., 2005; *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The ability of heavy chain-only antibodies devoid of light chain to bind antigen was established in the 1960s (Jaton et al. (1968) *Biochemistry,* 7, 4185-4195). Heavy chain immunoglobulin physically separated from light chain retained 80% of antigen-binding activity relative to the tetrameric antibody. Sitia et al. (1990) *Cell,* 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Brüggemann et al., *Crit. Rev. Immunol.;* 2006, 26(5):377-90; and Zou et al., 2007, *J Exp Med;* 204(13): 3271-3283. The production of knockout rats via embryo microinjections of zinc-finger nucleases is described in Geurts et al., 2009, *Science,* 325(5939):433. Soluble heavy chain-only antibodies and transgenic rodents comprising a heterologous heavy chain locus producing such antibodies are described in U. S. Pat. Nos. 8,883,150 and 9,365,655. CAR-T structures comprising single-domain antibodies as a binding (targeting) domain are described, for example, in Iri-Sofla et al., 2011, *Experimental Cell Research* 317:2630-2641 and Jamnani et al., 2014, *Biochim Biophys Acta,* 1840:378-386.

SUMMARY OF THE INVENTION

Aspects of the invention relate to heavy chain antibodies, including but not limited to UniAbs™, with binding affinity to CD19. Further aspects of the invention relate to methods of making such antibodies, compositions comprising such antibodies, and their use in the treatment of B-cell disorders that are characterized by the expression of CD19.

In some embodiments, a heavy chain-only antibody binding to CD19 comprises a heavy chain variable region comprising: (a) a CDR1 having two or fewer substitutions in any of the amino acid sequences of SEQ ID NOs: 1 to 6; and/or (b) a CDR2 having two or fewer substitutions in any of the amino acid sequences of SEQ ID NOs: 7 to 12; and/or (c) a CDR3 having two or fewer substitutions in the amino acid sequence of SEQ ID NO: 13. In some embodiments, the CDR1, CDR2, and CDR3 sequences are present in a human framework. In some embodiments, a heavy chain-only antibody further comprises a heavy chain constant region sequence in the absence of a CH1 sequence.

In some embodiments, a heavy chain-only antibody comprises: (a) a CDR1 sequence selected from the group consisting of SEQ ID NOs: 1 to 6; and/or (b) a CDR2 sequence selected from the group consisting of SEQ ID NOs: 7 to 12; and/or (c) a CDR3 sequence of SEQ ID NO: 13. In some embodiments, a heavy chain-only antibody comprises: (a) a CDR1 sequence selected from the group consisting of SEQ ID NOs: 1 to 6; and (b) a CDR2 sequence selected from the group consisting of SEQ ID NOs: 7 to 12; and (c) a CDR3 sequence of SEQ ID NO: 13.

In some embodiments, a heavy chain-only antibody comprises: (a) a CDR1 sequence of SEQ ID NO: 4, a CDR2 sequence of SEQ ID NO: 10, and a CDR3 sequence of SEQ ID NO: 13. In some embodiments, a heavy chain-only antibody comprises a heavy chain variable region having at least 95% sequence identity to any of the sequences of SEQ ID NOs: 14 to 21. In some embodiments, a heavy chain-only antibody comprises a heavy chain variable region sequence selected from the group consisting of SEQ ID NOs: 14 to 21. In some embodiments, a heavy chain-only antibody comprises a heavy chain variable region sequence of SEQ ID NO: 17.

In some embodiments, a heavy chain-only antibody binding to CD19 comprises a heavy chain variable region comprising (a) a CDR1 sequence of the formula:

$$\text{G F } X_1 \text{ F S } X_2 \text{ } X_3 \text{ W} \quad \text{(SEQ ID NO: 22)}$$

where $X_1$ is T or S; $X_2$ is S or N; $X_3$ is Y or F; and (b) a CDR2 sequence of the formula:

$$X_4 \text{ } X_5 \text{ } X_6 \text{ } X_7 \text{ G S } X_8 \text{ } X_9 \quad \text{(SEQ ID NO: 23)}$$

where $X_4$ is I or M; $X_5$ is N, S or K; $X_6$ is Q or K; $X_7$ is D or A; $X_8$ is D or E; $X_9$ is K or E; and (c) a CDR3 sequence of ASGVYSFDY (SEQ ID NO: 13).

In some embodiments, a heavy chain-only antibody binding to CD19 comprises a heavy chain variable region comprising CDR1, CDR2 and CDR3 sequences in a human VH framework, wherein the CDR sequences are sequences having two or fewer substitutions in a CDR sequence selected from the group consisting of SEQ ID NOs: 1-13.

In some embodiments, a heavy chain-only antibody comprises a heavy chain variable region comprising CDR1, CDR2 and CDR3 sequences in a human VH framework, wherein the CDR sequences are selected from the group consisting of SEQ ID NOs: 1-13.

In some embodiments, a heavy chain-only antibody binding to CD19 comprises a heavy chain variable region comprising: (a) a CDR1 sequence of SEQ ID NO: 4, a CDR2 sequence of SEQ ID NO: 10, and a CDR3 sequence of SEQ ID NO: 13, in a human VH framework.

In some embodiments, a heavy chain-only antibody is multi-specific. In some embodiments, a heavy chain-only antibody is bispecific. In some embodiments, a heavy chain-only antibody has binding affinity to two different CD19 proteins. In some embodiments, a heavy chain-only antibody has binding affinity to two different epitopes on the same CD19 protein. In some embodiments, a heavy chain-only antibody has binding affinity to an effector cell. In some embodiments, a heavy chain-only antibody has binding affinity to a T-cell antigen. In some embodiments, a heavy chain-only antibody has binding affinity to CD3. In some embodiments, a heavy chain-only antibody is in a CAR-T format.

Aspects of the invention relate to pharmaceutical compositions comprising a heavy chain-only antibody described herein.

Aspects of the invention relate to methods for the treatment of a B-cell disorder characterized by expression of CD19 comprising administering to a subject with said disorder an antibody or a pharmaceutical composition described herein. In some embodiments, the disorder is diffuse large B cell lymphoma (DLBCL). In some embodiments, the disorder is acute lymphoblastic leukemia (ALL). In some embodiments, the disorder is non-Hodgkin's lymphoma (NHL). In some embodiments, the disorder is systemic lupus erythematosus (SLE). In some embodiments, the disorder is rheumatoid arthritis (RA). In some embodiments, the disorder is multiple sclerosis (MS).

Aspects of the invention relate to polynucleotides encoding an antibody described herein, vectors comprising such polynucleotides, and cells comprising such vectors.

Aspects of the invention relate to methods of producing an antibody described herein, comprising growing a cell described herein under conditions permissive for expression of the antibody, and isolating the antibody from the cell and/or a cell culture medium in which the cell is grown.

Aspects of the invention relate to methods of making an antibody described herein, comprising immunizing a UniRat animal with CD19 and identifying CD19-binding heavy chain sequences.

Aspects of the invention relate to methods of treatment, comprising administering to an individual in need an effective dose of an antibody or pharmaceutical composition as described herein.

Aspects of the invention relate to use of an antibody or pharmaceutical composition as described herein in the preparation of a medicament for the treatment of a disease or disorder in an individual in need.

Aspects of the invention relate to a kit for treating a disease or disorder in an individual in need, comprising an antibody or pharmaceutical composition as described herein, and instructions for use. In some embodiments, a kit further comprises at least one additional reagent. In some embodiments, the at least one additional reagent comprises a chemotherapeutic drug.

These and further aspects will be further explained in the rest of the disclosure, including the Examples.

BRIEF DESCRIPTION OF THE DRAWINGS

FIG. 1 shows anti-CD19 heavy chain antibody unique CDR amino acid sequences.

FIG. 2 shows anti-CD19 heavy chain antibody variable domain amino acid sequences.

FIG. 3 shows anti-CD19 heavy chain antibody CDR1, CDR2 and CDR3 amino acid sequences.

FIG. 4 shows anti-CD19 heavy chain antibody biological activities.

DETAILED DESCRIPTION OF THE PREFERRED EMBODIMENTS

Figure 5A:
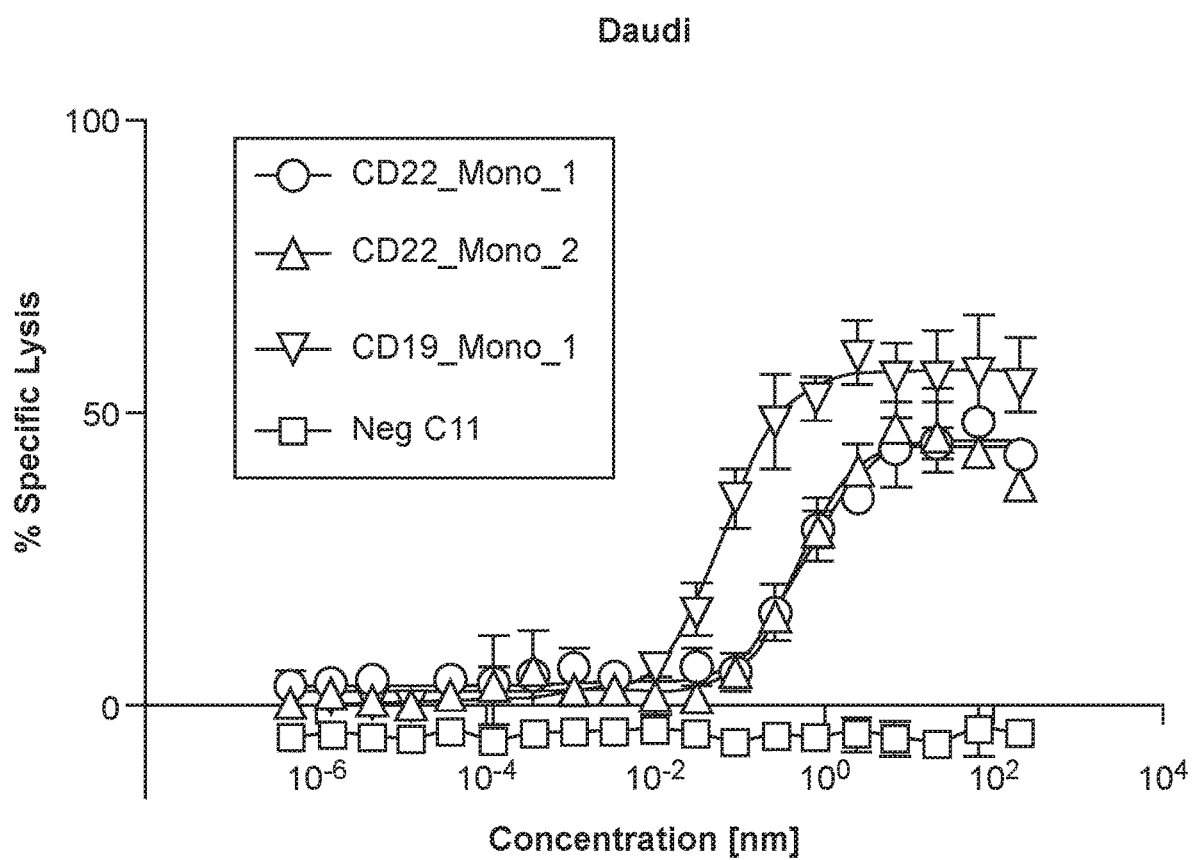
FIG. 5A is a graph depicting percent specific lysis as a function of antibody concentration.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

Antibodies, also referred to as immunoglobulins, conventionally comprise at least one heavy chain and one light chain, where the amino terminal domain of the heavy and light chains is variable in sequence, hence is commonly referred to as a variable region domain, or a variable heavy (VH) or variable light (VH) domain. The two domains conventionally associate to form a specific binding region, although as will be discussed here, specific binding can also be obtained with heavy chain-only variable sequences, and a variety of non-natural configurations of antibodies are known and used in the art.

A "functional" or "biologically active" antibody or antigen-binding molecule (including heavy chain-only antibodies and multi-specific (e.g., bispecific) three-chain antibody-like molecules (TCAs), described herein) is one capable of exerting one or more of its natural activities in structural, regulatory, biochemical or biophysical events. For example, a functional antibody or other binding molecule, e.g., a TCA, may have the ability to specifically bind an antigen and the binding may in turn elicit or alter a cellular or molecular event such as signal transduction or enzymatic activity. A functional antibody or other binding molecule, e.g., a TCA, may also block ligand activation of a receptor or act as an agonist or antagonist. The capability of an antibody or other binding molecule, e.g., a TCA, to exert one or more of its natural activities depends on several factors, including proper folding and assembly of the polypeptide chains The term "antibody" herein is used in the broadest sense and specifically covers monoclonal antibodies, polyclonal antibodies, monomers, dimers, multimers, multispecific antibodies (e.g., bispecific antibodies), heavy chain-only antibodies, three chain antibodies, single chain Fv (scFv), nanobodies, etc., and also includes antibody fragments, so long as they exhibit the desired biological activity (Miller et al (2003) Jour. of Immunology 170:4854-4861). Antibodies may be murine, human, humanized, chimeric, or derived from other species.

The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof, such targets including but not limited to, a cancer cell, or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. The immunoglobulins can be derived from any species. In one aspect, the immunoglobulin is of largely human origin.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies in accordance with the present invention can be made by the hybridoma method first described by Kohler et al. (1975) *Nature* 256:495, an can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" residues 26-32 (H1), 53-55 (H2) and 96-101 (H3) in the heavy chain variable domain; Chothia and Lesk *J. Mol. Biol.* 196:901-917 (1987)).

"Framework Region" or "FR" residues are those variable domain residues other than the hypervariable region residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." *Mol Immunol.* 2010; 47:694-700), which is based on sequence variability and is the most commonly used. The Chothia definition is based on the location of the structural loop regions (Chothia et al. "Conformations of immunoglobulin hypervariable regions." *Nature.* 1989; 342:877-883). Alternative CDR definitions of interest include, without limitation, those disclosed by Honegger, "Yet another numbering scheme for immunoglobulin variable domains: an automatic modeling and analysis tool." *J Mol Biol.* 2001; 309:657-670; Ofran et al. "Automated identification of complementarity determining regions (CDRs) reveals peculiar characteristics of CDRs and B cell epitopes." *J Immunol.* 2008; 181:6230-6235; Almagro "Identification of differences in the specificity-determining residues of antibodies that recognize antigens of different size: implications for the rational design of antibody repertoires." *J Mol Recognit.* 2004; 17:132-143; and Padlanet al. "Identification of specificity-determining residues in antibodies." Faseb J. 1995; 9:133-139., each of which is herein specifically incorporated by reference.

The terms "heavy chain-only antibody," and "heavy-chain antibody" are used interchangeably herein and refer, in the broadest sense, to antibodies lacking the light chain of a conventional antibody. The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs™). In one embodiment, a heavy chain-only antibody is composed of the variable region antigen-binding domain composed of framework 1, CDR1, framework 2, CDR2, framework 3, CDR3, and framework 4. In another embodiment, the heavy chain-only antibody is composed of an antigen-binding domain, at least part of a hinge region and CH2 and CH3 domains. In another embodiment, the heavy chain-only antibody is composed of an antigen-binding domain, at least part of a hinge region and a CH2 domain. In a further embodiment, the heavy chain-only antibody is composed of an antigen-binding domain, at least part of a hinge region and a CH3 domain. Heavy chain-only antibodies in which the CH2 and/or CH3 domain is truncated are also included herein. In a further embodiment the heavy chain is composed of an antigen binding domain, and at least one CH (CH1, CH2, CH3, or CH4) domain but no hinge region. In a further embodiment the heavy chain is composed of an antigen binding domain, at least one CH (CH1, CH2, CH3, or CH4) domain, and at least a portion of a hinge region. The heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, the heavy-chain antibody is of the IgG1, IgG2, IgG3, or IgG4 subtype, in particular the IgG1 subtype. In one embodiment, the heavy-chain antibody is of the IgG4 subtype, wherein one or more of the CH domains are modified to alter an effector function of the antibody. In one embodiment, the heavy-chain antibody is of the IgG1 subtype, wherein one or more of the CH domains are modified to alter an effector function of the antibody. Modifications of CH domains that alter effector function are further described herein. Non-limiting examples of heavy-chain antibodies are described, for example, in WO2018/039180, the disclosure of which is incorporated herein by reference in its entirety.

In one embodiment, the heavy chain-only antibodies herein are used as a binding (targeting) domain of a chimeric antigen receptor (CAR). The definition specifically includes human heavy chain-only antibodies produced by human immunoglobulin transgenic rats (UniRat™), called UniAbs™. The variable regions (VH) of UniAbs™ are called UniDabs™, and are versatile building blocks that can be linked to Fc regions or serum albumin for the development of novel therapeutics with multi-specificity, increased potency and extended half-life. Since the homodimeric UniAbs™ lack a light chain and thus a VL domain, the antigen is recognized by one single domain, i.e., the variable domain (antigen-binding domain) of the heavy chain of a heavy-chain antibody (VH).

An "intact antibody chain" as used herein is one comprising a full length variable region and a full length constant region (Fc). An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains (including, e.g., a CH4 domain) The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) *Eur. J. Biochem.* 267:7246-7256; US 2005/0048572; US 2004/0229310). The light chains of antibodies from any vertebrate species can be assigned to one of two types, called κ (kappa) and λ (lambda), based on the amino acid sequences of their constant domains.

A "functional Fc region" possesses an "effector function" of a native-sequence Fc region. Non-limiting examples of effector functions include C1q binding; CDC; Fc-receptor binding; ADCC; ADCP; down-regulation of cell-surface receptors (e.g., B-cell receptor), etc. Such effector functions generally require the Fc region to interact with a receptor, e.g., the FcγRI; FcγRIIA; FcγRIIB1; FcγRIIB2; FcγRIIIA; FcγRIIIB receptors, and the low affinity FcRn receptor; and can be assessed using various assays known in the art. A "dead" or "silenced" Fc is one that has been mutated to retain activity with respect to, for example, prolonging serum half-life, but which does not activate a high affinity Fc receptor, or which has a reduced affinity to an Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences may include three amino acid substitutions in the CH2 region to reduce FcγRI binding at EU index positions 234, 235, and 237 (see Duncan et al., (1988) Nature 332:563). Two amino acid substitutions in the complement C1q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 or IgG2 residues at positions 233-236 and IgG4 residues at positions 327, 330 and 331 greatly reduces ADCC and CDC (see, for example, Armour KL. et al., 1999 Eur J Immunol. 29(8): 2613-24; and Shields RL. et al., 2001. J Biol Chem. 276 (9):6591-604). The human IgG1 amino acid sequence (UniProtKB No. P01857) is provided herein as SEQ ID NO: 26. The human IgG4 amino acid sequence (UniProtKB No. P01861) is provided herein as SEQ ID NO: 27. Silenced IgG1 is described, for example, in Boesch, A.W., et al., "Highly parallel characterization of IgG Fc binding interactions." MAbs, 2014. 6(4): p. 915-27, the disclosure of which is incorporated herein by reference in its entirety.

Other Fc variants are possible, including, without limitation, one in which a region capable of forming a disulfide bond is deleted, or in which certain amino acid residues are eliminated at the N-terminal end of a native Fc, or a methionine residue is added thereto. Thus, in some embodiments, one or more Fc portions of a binding compound can comprise one or more mutations in the hinge region to eliminate disulfide bonding. In yet another embodiment, the hinge region of an Fc can be removed entirely. In still another embodiment, a binding compound can comprise an Fc variant.

Further, an Fc variant can be constructed to remove or substantially reduce effector functions by substituting (mutating), deleting or adding amino acid residues to effect complement binding or Fc receptor binding. For example, and not limitation, a deletion may occur in a complement-binding site, such as a C1q-binding site. Techniques for preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, an antibody having an Fc region according to this invention can comprise an antibody with or without K447.

Aspects of the invention include binding compounds having multi-specific configurations, which include, without limitation, bispecific, trispecific, etc. A large variety of methods and protein configurations are known and used in bispecific monoclonal antibodies (BsMAB), tri-specific antibodies, etc.

Various methods for the production of multivalent artificial antibodies have been developed by recombinantly fusing variable domains of two or more antibodies. In some embodiments, a first and a second antigen-binding domain on a polypeptide are connected by a polypeptide linker. One non-limiting example of such a polypeptide linker is a GS linker, having an amino acid sequence of four glycine residues, followed by one serine residue, and wherein the sequence is repeated n times, where n is an integer ranging from 1 to about 10, such as 2, 3, 4, 5, 6, 7, 8, or 9. Non-limiting examples of such linkers include GGGGS (SEQ ID NO: 24) (n=1) and GGGGSGGGGS (SEQ ID NO: 25) (n=2). Other suitable linkers can also be used, and are described, for example, in Chen et al., Adv Drug Deliv Rev. 2013 Oct. 15; 65(10): 1357-69, the disclosure of which is incorporated herein by reference in its entirety.

The term "three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy-chain only antibody comprising an Fc portion comprising CH2 and/or CH3 and/or CH4 domains, in the absence of a CH1 domain, and one or more antigen binding domains (e.g., a single heavy chain variable region (a "single configuration"), or two antigen binding domains (e.g., two single heavy chain variable regions) in a "tandem configuration", where the two antigen binding domains are linked together by a linker sequence, as described above) that binds an epitope of a second antigen or a different epitope of the first antigen, where such binding domain is derived from or has sequence identity with the variable region of an antibody heavy or light chain Parts of such variable region may be encoded by $V_H$ and/or $V_L$ gene segments, D and $J_H$ gene segments, or $J_L$ gene segments. The variable region may be encoded by rearranged $V_H D J_H$, $V_L D J_H$, $V_H J_L$, or $V_L J_L$ gene segments. A TCA protein makes use of a heavy chain-only antibody as hereinabove defined.

A TCA binding compound makes use of a "heavy chain only antibody" or "heavy chain antibody" or "heavy chain polypeptide" which, as used herein, mean a single chain antibody comprising heavy chain constant regions CH2 and/or CH3 and/or CH4, but no CH1 domain. In one embodiment, the heavy chain antibody is composed of an antigen-binding domain (e.g., a single heavy chain variable region, in a single or tandem configuration), at least part of a hinge region and CH2 and CH3 domains.

In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain. Heavy chain antibodies in which the CH2 and/or CH3 domain is truncated are also included herein. In a further embodiment, the heavy chain is composed of an antigen binding domain, and at least one CH (CH1, CH2, CH3, or CH4) domain but no hinge region. The heavy chain only antibody can be in the form of a dimer, in which two heavy chains are disulfide bonded other otherwise covalently or non-covalently attached with each other, and can optionally include an asymmetric interface between two or more of the CH domains to facilitate proper pairing between polypeptide chains. The heavy-chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype or the IgG4 subtype. Non-limiting examples of a TCA binding compound are described in, for example, WO2017/223111 and WO2018/052503, the disclosures of which are incorporated herein by reference in their entirety.

Heavy-chain antibodies constitute about one fourth of the IgG antibodies produced by the camelids, e.g., camels and llamas (Hamers-Casterman C., et al. Nature. 363, 446-448 (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. J. Biol. Chem. 276, 26285-26290 (2001)). Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)). Sharks have also been shown to have a single VH-like domain in their antibodies, termed VNAR. (Nuttall et al. Eur. J. Biochem. 270, 3543-3554 (2003); Nuttall et al. Function and Bioinformatics 55, 187-197 (2004); Dooley et al., Molecula Immunology 40, 25-33 (2003)).

The terms "CD19" and "cluster of differentiation 19" as used herein refer to a molecule expressed during all phases of B cell development until terminal differentiation into plasma cells. The term "CD19" includes a CD19 protein of any human and non-human animal species, and specifically includes human CD19 as well as CD19 of non-human mammals The term "human CD19" as used herein includes any variants, isoforms and species homologs of human CD19 (UniProt P15391), regardless of its source or mode of preparation. Thus, "human CD19" includes human CD19 naturally expressed by cells and CD19 expressed on cells transfected with the human CD19 gene.

The terms "anti-CD19 heavy chain-only antibody," "CD19 heavy chain-only antibody," "anti-CD19 heavy chain antibody" and "CD19 heavy chain antibody" are used herein interchangeably to refer to a heavy chain-only antibody as hereinabove defined, immuno specifically binding to CD19, including human CD19, as hereinabove defined. The definition includes, without limitation, human heavy chain antibodies produced by transgenic animals, such as transgenic rats or transgenic mice expressing human immunoglobulin, including UniRats™ producing human anti-CD19 UniAb™ antibodies, as hereinabove defined.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. The terms "multi-specific antibody," "multi-specific heavy chain-only antibody," "multi-specific heavy chain antibody," "multi-specific UniAb™", and "multi-specific binding compound" are used herein in the broadest sense and cover all antibodies with more than one binding specificity. The multi-specific heavy chain anti-CD19 antibodies of the present invention specifically include antibodies immunospecifically binding to one single epitope on a CD19 protein, such as a human CD19, and to an epitope on a different protein, such as, for example, a CD3 protein (i.e., bivalent and monoparatopic). The multi-specific heavy chain anti-CD19 antibodies of the present invention specifically include antibodies immunospecifically binding to two or more non-overlapping epitopes on a CD19 protein, such as a human CD19 (i.e., bivalent and biparatopic). The multi-specific heavy chain anti-CD19 antibodies of the present invention also specifically include antibodies immunospecifically binding to an epitope on a CD19 protein, such as human CD19 and to an epitope on a different protein, such as, for example, a CD3 protein, such as human CD3 (i.e., bivalent and biparatopic). The multi-specific heavy chain anti-CD19 antibodies of the present invention also specifically include antibodies immunospecifically binding to two or more non-overlapping or partially overlapping epitopes on a CD19 protein, such as a human CD19 protein, and to an epitope on a different protein, such as, for example, a CD3 protein, such as human CD3 protein (i.e., trivalent and biparatopic).

Antibodies of the invention include monospecific antibodies, having one binding specificity. Monospecific antibodies specifically include antibodies comprising a single binding specificity, as well as antibodies comprising more than one binding unit having the same binding specificity. The terms "monospecific antibody," "monospecific heavy chain-only antibody," "monospecific heavy chain antibody," and "monospecific UniAb™" are used herein in the broadest sense and cover all antibodies with one binding specificity. The monospecific heavy chain anti-CD19 antibodies of the present invention specifically include antibodies immunospecifically binding to one epitope on a CD19 protein, such as a human CD19 (monovalent and monospecific). The monospecific heavy chain anti-CD19 antibodies of the present invention also specifically include antibodies having more than one binding unit (e.g., multivalent antibodies) immunospecifically binding to an epitope on a CD19 protein, such as human CD19. For example, a monospecific antibody in accordance with embodiments of the invention can include a heavy chain variable region comprising two antigen-binding domains, wherein each antigen-binding domain binds to the same epitope on a CD19 protein (i.e., bivalent and monospecific).

An "epitope" is the site on the surface of an antigen molecule to which a single antibody molecule binds. Generally, an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present invention specifically includes anti-CD19 heavy chain antibodies with polyepitopic specificities, i.e., anti-CD19 heavy chain antibodies binding to two or more non-overlapping epitopes on a CD19 protein, such as a human CD19. The term "non-overlapping epitope(s)" or "non-competitive epitope(s)" of an antigen is defined herein to mean epitope(s) that are recognized by one member of a pair of antigen-specific antibodies, but not the other member. Pairs of antibodies, or antigen-binding regions targeting the same antigen on a multi-specific antibody, recognizing non-overlapping epitopes do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "monovalent" antibody has one binding site. Thus a monovalent antibody is also monospecific.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent. A bivalent antibody in accordance with embodiments of the invention may have two binding sites to the same epitope (i.e., bivalent, monoparatopic), or to two different epitopes (i.e., bivalent, biparatopic).

A large variety of methods and protein configurations are known and used for the preparation of bispecific monoclonal antibodies (BsMAB), tri-specific antibodies, and the like.

The term "bispecific three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain-only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain Parts of such variable region may be encoded by VH and/or VL gene segments, D and $J_H$ gene segments, or JL gene segments. The variable region may be encoded by rearranged $V_HDJ_H$, $V_LDJ_H$, $V_HJ_L$, or $V_LJ_L$ gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T cell to create a chimeric antigen receptor (CAR). (Dai et al., *J Natl Cancer Inst*, 2016; 108(7):djv439; and Jackson et al., *Nature Reviews Clinical Oncology*, 2016; 13:370-383.).

The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and-macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T cell receptors or FcRs and perform effector functions. Preferably, the cells express at least FcγRIII and perform ADCC effector function. Examples of human leukocytes which mediate ADCC include natural killer (NK) cells, monocytes, cytotoxic T cells and neutrophils; with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B cells and T cells including cytolytic T cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (*USA*) 95:652-656 (1998).

"Complement dependent cytotoxicity" or "CDC" refers to the ability of a molecule to lyse a target in the presence of complement. The complement activation pathway is initiated by the binding of the first component of the complement system (Clq) to a molecule (e.g., an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, CA) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen*, 12(8), 791-800, 2009).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "B-cell neoplasms" or "mature B-cell neoplasms" in the context of the present invention include, but are not limited to, all lymphoid leukemias and lymphomas, chronic lymphocytic leukemia, acute lymphoblastc leukemia, prolymphocytic leukemia, precursor B-lymphoblastic leukemia, hair cell leukemia, small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma (DLBCL), multiple myeloma, lymphoplasmacytic lymphoma, splenic marginal zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

The term "characterized by expression of CD19" broadly refers to any disease or disorder in which CD19 expression is associated with or involved with one or more pathological processes that are characteristic of the disease or disorder. Such disorders include, but are not limited to, B-cell neoplasms.

The terms "subject," "individual," and "patient" are used interchangeably herein to refer to a mammal being assessed for treatment and/or being treated. In an embodiment, the mammal is a human The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0 ° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomeriation), clipping/hydrolysis/fragmentation (e.g., hinge region fragmentation), succinimide formation, unpaired cysteine(s), N-terminal extension, C-terminal processing, glycosylation differences, etc.

II Detailed Description

Anti-CD19 Antibodies

The present invention provides a family of closely related heavy chain-only antibodies that bind to human CD19. The antibodies of this family comprise a set of CDR sequences as defined herein and shown in FIG. 1, and are exemplified by the provided heavy chain variable region (VH) sequences of SEQ ID NOs: 14 to 21 set forth in FIG. 2. The families of antibodies provide a number of benefits that contribute to utility as clinically therapeutic agent(s). The antibodies include members with a range of binding affinities, allowing the selection of a specific sequence with a desired binding affinity.

Figure 5B:
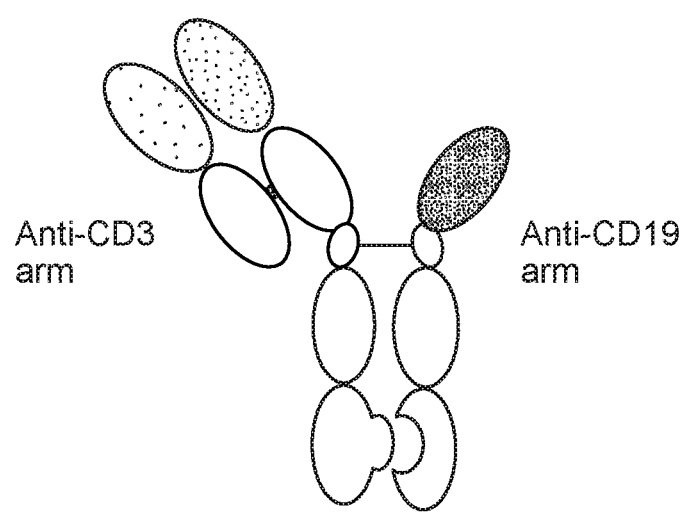
FIG. 5B is a schematic illustration of a bispecific anti-CD19 x anti-CD3 in accordance with one embodiment of the invention.

A suitable antibody may be selected from those provided herein for development and therapeutic or other use, including, without limitation, use as a bispecific antibody, e.g., as shown in FIG. 5B, or tri-specific antibody, or part of a CAR-T structure.

Determination of affinity for a candidate protein can be performed using methods known in the art, such as Biacore measurements. Members of the antibody family may have an affinity for CD19 with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a CD19 biological activity, including in vitro assays, pre-clinical models, and clinical trials, as well as assessment of potential toxicity.

Members of the antibody family herein are not cross-reactive with the CD19 protein of *Cynomolgus* macaque, but can be engineered to provide cross-reactivity with the CD19 protein of *Cynomolgus* macaque, or with the CD19 of any other animal species, if desired.

The family of CD19-specific antibodies herein comprises a VH domain, comprising CDR1, CDR2 and CDR3 sequences in a human VH framework. The CDR sequences may be situated, as an example, in the region of around amino acid residues 26-35; 53-59; and 98-117 for CDR1, CDR2 and CDR3, respectively, of the provided exemplary variable region sequences set forth in SEQ ID NOs: 14 to 21. It will be understood by one of ordinary skill in the art that the CDR sequences may be in different positions if a different framework sequence is selected, although generally the order of the sequences will remain the same.

The CDR1, CDR2, and CDR3 sequences of the anti-CD19 antibodies of the present invention may be encompassed by the following structural formulas, where an X indicates a variable amino acid, which may be any of the specific amino acids indicated below.

```
CDR1
                                    (SEQ ID NO: 22)
G F X₁ F S X₂ X₃ W
where X₁ is T or S;
X₂ is S or N; and
X₃ is Y or F.

CDR2
                                    (SEQ ID NO: 23)
X₄ X₅ X₆ X₇ G S X₈ X₉
where X4 is I or M;
X₅ is N, S or K;
X₆ is Q or K;
X₇ is D or A;
X₈ is D or E; and
X₉ is K or E.

CDR3
                                    (SEQ ID NO: 13)
ASGVYSFDY
```

Representative CDR1, CDR2 and CDR3 sequences are shown in FIG. 1 and FIG. 3.

In some embodiments, an anti-CD19 heavy chain-only antibody of the invention comprises a CDR1 sequence of any one of SEQ ID NOs: 1-6. In a particular embodiment, the CDR1 sequence is SEQ ID NO: 4.

In some embodiments, an anti-CD19 heavy chain-only antibody of the invention comprises a CDR2 sequence of any one of SEQ ID NOs: 7-12. In a particular embodiment, the CDR2 sequence is SEQ ID NO: 10.

Anti-CD19 heavy chain-only antibodies of the invention comprises a CDR3 sequence of SEQ ID NO: 13.

In a further embodiment, an anti-CD19 heavy chain-only antibody of the invention comprises the CDR1 sequence of SEQ ID NO: 4; the CDR2 sequence of SEQ ID NO: 10; and the CDR3 sequence of SEQ ID NO: 13.

In further embodiments, an anti-CD19 heavy chain-only antibody of the invention comprises any of the heavy chain variable region amino acid sequences of SEQ ID NOs: 14 to 21 (FIG. 2).

In a still further embodiment, an anti-CD19 heavy chain-only antibody of the present invention comprises the heavy chain variable region sequence of SEQ ID NO: 17.

In some embodiments, a CDR sequence in an anti-CD19 heavy chain-only antibody of the invention comprises one or two amino acid substitutions relative to a CDR1, CDR2 and/or CDR3 sequence or set of CDR1, CDR2 and CDR3 sequences in any one of SEQ ID NOs: 1 to 13 (FIG. 1). In some embodiments, the heavy chain-only anti-CD19 antibodies herein will comprise a heavy chain variable region sequence with at least about 85% identity, at least 90% identity, at least 95% identity, at least 98% identify, or at least 99% identity to any of the heavy chain variable region sequences of SEQ ID NOs: 14 to 21 (shown in FIG. 2).

In some embodiments, bispecific or multispecific antibodies are provided, which may have any of the configurations discussed herein, including, without limitation, a bispecific three-chain antibody-like molecule. In some embodiments, a bispecific antibody can comprise at least one heavy chain variable region having binding specificity for CD19, and at least one heavy chain variable region having binding specificity for a protein other than CD19. In some embodiments, a bispecific antibody can comprise a heavy chain/light chain pair that has binding specificity for a first antigen, and a heavy chain from a heavy chain-only antibody, comprising an Fc portion comprising CH2 and/or CH3 and/or CH4 domains, in the absence of a CH1 domain, and an antigen binding domain that binds an epitope of a second antigen or a different epitope of the first antigen. In one particular embodiment, a bispecific antibody comprises a heavy chain/light chain pair that has binding specificity for an antigen on an effector cell (e.g., a CD3 protein on a T cell), and a heavy chain from a heavy chain-only antibody comprising an antigen-binding domain that has binding specificity for CD 19.

In some embodiments, where a protein of the invention is a bispecific antibody, one arm of the antibody (one binding moiety) is specific for human CD19, while the other arm may be specific for target cells, tumor-associated antigens, targeting antigens, e.g., integrins, etc., pathogen antigens, checkpoint proteins, and the like. Target cells specifically include cancer cells, including, without limitation, cells from hematologic tumors, e.g., B-cell tumors, as discussed below.

In some embodiments, a protein of the invention comprises any one of the Fc region sequences provided below, which correspond to native sequence human IgG1, native sequence human IgG4, variant sequence human IgG1 which has been engineered to reduce one or more effector functions, and variant sequence human IgG4 which has been engineered to reduce one or more effector functions.

expressed on mature B-cells, and CD3 (anti-CD19 ×anti-CD3 antibodies). Such antibodies induce potent T cell mediated killing of cells expressing CD19.

Preparation of Anti-CD19 Heavy Chain Antibodies

The heavy chain antibodies of the present invention can be prepared by methods known in the art. In a preferred embodiment, the heavy chain antibodies herein are produced by transgenic animals, including transgenic mice and rats, preferably rats, in which the endogenous immunoglobulin genes are knocked out or disabled. In a preferred embodiment, the heavy chain antibodies herein are produced in UniRat™. UniRat™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety technologies, in UniRat™ the zinc-finger (endo) nuclease (ZNF) technology was used to inactivate the endogenous rat heavy chain J-locus, light chain $C_\kappa$ locus and light chain $C_\lambda$ locus. ZNF constructs for microinjection into oocytes can produce IgH and IgL knock out (KO) lines. For details see, e.g., Geurts et al., 2009, Science 325:433. Characterization of Ig heavy chain knockout rats has been reported by Menoret et al., 2010, Eur. J. Immunol. 40:2932-

TABLE 1

Human IgG1 and IgG4 Fc region sequences.

| | |
|---|---|
| Human IgG1 (UniProtNo. P01857) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGK (SEQ ID NO: 26) |
| Human IgG4 (UniProt No. P01861) | ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPSCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK (SEQ ID NO: 27) |
| Human IgG1 with silencing mutation (Fc region) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPEAAGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 28) |
| Human IgG4 with Silencing mutation (Fc region) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPCPAPEAAGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLY SRLTVDKSRWQEGNVFSCSVMHEALHNHYTQKSLSLSLGK (SEQ ID NO: 29) |

Various formats of bispecific antibodies are within the ambit of the invention, including, without limitation, single chain polypeptides, two chain polypeptides, three chain polypeptides, four chain polypeptides, and multiples thereof. The bispecific antibodies herein specifically include T cell bispecific antibodies binding to CD19, which is selectively 2941. Advantages of the ZNF technology are that non-homologous end joining to silence a gene or locus via deletions up to several kb can also provide a target site for homologous integration (Cui et al., 2011, Nat Biotechnol 29:64-67). Human heavy chain antibodies produced in UniRat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, rat can also be used, rats and mice being preferred. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), E. coli or yeast.

Domains of heavy chain-only antibodies combine advantages of antibodies and small molecule drugs: can be mono- or multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost-effective manner.

In a particular embodiment, the heavy chain antibodies of the present invention, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. The substituted amino acid residue preferably is charged, and more preferably is positively charged, such as lysine (Lys, K), arginine (Arg, R) or histidine (His, H), preferably arginine (R). In a preferred embodiment the heavy chain-only antibodies derived from the transgenic animals contain a Trp to Arg mutation at position 101. The resultant HCAbs preferably have high antigen-binding affinity and solubility under physiological conditions in the absence of aggregation.

As part of the present invention, human IgG anti-CD19 heavy chain antibodies with unique sequences from UniRat™ animals (UniAb™) were identified that bind human CD19 in ELISA (recombinant CD19 extracellular domain) protein and cell-binding assays. The identified heavy chain variable region (VH) sequences (see FIG. 2) are positive for human CD19 protein binding and/or for binding to CD19+ cells, and are all are negative for binding to cells that do not express CD19.

The antibodies described herein bind CD19-positive Burkitt's lymphoma cell lines Daudi (ATCC® CCL-213™), Raji (ATCC® CCL-86™), and Ramos (ATCC® CRL-1596™), and some are cross-reactive with the CD19 protein of Cynomolgus macaque. In addition, they can be engineered to provide cross-reactivity with the CD19 protein of any animal species, if desired.

The anti-CD19 heavy chain antibodies, such as UniAbs™ herein may have an affinity for CD19 with a Kd of from about $10^{-6}$ to around about $10^{11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a CD19 biological activity, including in vitro assays, pre-clinical models, and clinical trials, as well as assessment of potential toxicity.

Heavy chain antibodies binding to non-overlapping epitopes on a CD19 protein, e.g., UniAbs™ can be identified by competition binding assays, such as enzyme-linked immunoassays (ELISA assays) or flow cytometric competitive binding assays. For example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn XPR36 (BioRad, Inc), Biacore 2000 and Biacore T200 (GE Healthcare Life Sciences), and MX96 SPR imager (Ibis technologies B. V.), as well as on biolayer interferometry platforms, such as Octet Red384 and Octet HTX (ForteBio, Pall Inc). For further details see the examples herein.

Typically, an antibody "competes" with a reference antibody if it causes about 15-100% reduction in the binding of the reference antibody to the target antigen, as determined by standard techniques, such as by the competition binding assays described above. In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, at least about 95% or higher.

Pharmaceutical Compositions, Uses and Methods of Treatment

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

In one embodiment, a pharmaceutical composition comprises a heavy chain antibody (e.g., UniAb™) that binds to CD19. In another embodiment, a pharmaceutical composition comprises a multi-specific (including bispecific) heavy chain antibody (e.g., UniAb™) with binding specificity for two or more non-overlapping epitopes on a CD19 protein. In a preferred embodiment, a pharmaceutical composition comprises a multi-specific (including bispecific) heavy chain antibody (e.g., UniAb™) with binding specificity to CD19 and with binding specificity to a binding target on an effector cell (e.g., a binding target on a T cell, such as, e.g., a CD3 protein on a T cell).

Pharmaceutical compositions of the antibodies used in accordance with the present invention are prepared for storage by mixing proteins having the desired degree of purity with optional pharmaceutically acceptable carriers, excipients or stabilizers (see, e.g., Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Antibody formulations are disclosed, for example, in U.S. Patent No. 9,034,324. Similar formulations can be used for the heavy chain antibodies, including UniAbs™, of the present invention. Subcutaneous antibody formulations are described, for example, in US20160355591 and US20160166689.

Methods of Use

The heavy chain-only anti-CD19 antibodies, multi-specific antibodies, and pharmaceutical compositions described herein can be used for the treatment of diseases and conditions characterized by the expression of CD19, including, without limitation, the conditions and diseases described further herein.

CD19 is a cell surface receptor that is expressed on all human B-cells, but is not found on plasma cells. It has a relatively large, 240 amino acid, cytoplasmic tail. The extracellular Ig-like domains are divided by a potential disulfide linked non-Ig-like domain and N-linked carbohydrate addition sites. The cytoplasmic tail contains at least nine tyrosine residues near the C-terminus, some of which have been shown to be phosphorylated. Along with CD20 and CD22, the restricted expression of CD19 to the B-cell lineage makes it an attractive target for the therapeutic treatment of B-cell malignancies. Due to its observed expression in a number of hematological malignancies, CD19 is a promising target for antibody-based therapeutics.

In one aspect, the CD19 heavy chain antibodies (e.g., UniAbs™) and pharmaceutical compositions herein can be used to treat hematological malignancies characterized by the expression of CD19, including, without limitation, diffuse large B cell lymphoma (DLBCL), non-Hodgkin's lymphoma, B-cell chronic lymphocylic leukemia (CLL), and B-cell acute lymphoblastic leukemia (ALL).

Diffuse large B cell lymphoma (DLBCL or DLBL) is the most common form of non-Hodgkin's lymphoma among adults (Blood 1997 89 (11): 3909-18), with an estimated annual incidence of 7 to 8 cases per 100,000 people per year in the US and the UK. It is characterized as an aggressive cancer that can arise in virtually any part of the body. The causes of DLBCL are not well understood, and it can arise from normal B cells as well as malignant transformation of other types of lymphoma or leukemia cells. Treatment approaches generally involve chemotherapy and radiation, and have resulted in an overall five-year survival rate average of approximately 58% for adults. Although some monoclonal antibodies have shown promise for treating DLBCL, consistent clinical efficacy has not yet been conclusively demonstrated. There is therefore a great need for new therapies, including immunotherapies, for DLBCL.

In another aspect, the CD19 heavy chain antibodies (e.g., UniAbs™) and pharmaceutical compositions herein can be used to treat autoimmune disorders characterized by pathogenic B-cells that express CD19, including, without limitation, systemic lupus erythematosus (SLE), rheumatoid arthritis (RA), and multiple sclerosis (MS).

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but non-human mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage of the agent may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for their use. A kit can further contain at least one additional reagent, e.g., a chemotherapeutic drug, etc. Kits typically include a label indicating the intended use of the contents of the kit. The term "label" as used herein includes any writing, or recorded material supplied on or with a kit, or which otherwise accompanies a kit.

The invention now being fully described, it will be apparent to one of ordinary skill in the art that various changes and modifications can be made without departing from the spirit or scope of the invention.

EXAMPLES

Materials and Methods
CD19 Cell Binding

Binding to CD19 positive cells was assessed by flow cytometry (Guava easyCyte 8HT, EMD Millipore) using the Daudi cell line (ATCC). Briefly, 100,000 target cells were stained with a dilution series of purified UniAbs™ for 30 minutes at 4° C. Following incubation, the cells were washed twice with flow cytometry buffer (1X PBS, 1% BSA, 0.1% NaN$_3$) and stained with goat F(ab')$_2$ anti-human IgG conjugated to R-phycoerythrin (PE) (Southern Biotech, cat. #2042-09) to detect cell-bound antibodies. After a 20-minute incubation at 4° C., the cells were washed twice with flow cytometry buffer and then mean fluorescence intensity (MFI) was measured by flow cytometry. EC50 values were calculated using GraphPad Prism 7. Binding to cynomolgus CD19 positive cells was determined using the same protocol with the following modifications: the target cells were from CHO cells stably transfected to express the extracellular domain of cynomolgus CD19 and each antibody was tested at a single concentration (~1.7 µg/mL) so EC50 values were not calculated.

Example 1

Genetically Engineered Rats Expressing Heavy Chain-Only Antibodies

A 'human—rat' IgH locus was constructed and assembled in several parts. This involved the modification and joining of rat C region genes downstream of human JHs and subsequently, the upstream addition of the human $V_H6$—D-segment region. Two BACs with separate clusters of human $V_H$ genes [BAC6 and BAC3] were then co-injected with the BAC termed Georg, encoding the assembled and modified region comprising human $V_H6$, all Ds, all $J_H$s, and modified rat Cγ2a/1/2b ($\Delta C_H1$).

Transgenic rats carrying artificial heavy chain immunoglobulin loci in unrearranged configuration were generated. The IgG2a($\Delta C_H1$)., IgG1($\Delta C_H1$)., IgG2b($\Delta C_H1$) genes lacked the $C_H1$ segment. The constant region genes IgE, IgA and 3' enhancer were included in Georg BAC. RT-PCR and serum analysis (ELISA) of transgenic rats revealed productive rearrangement of transgenic immunoglobulin loci and expression of heavy chain-only antibodies of various isotypes in serum. Transgenic rats were cross-bred with rats with mutated endogenous heavy chain and light chain loci previously described in US patent publication 2009/0098134 A1. Analysis of such animals demonstrated inactivation of rat immunoglobulin heavy and light chain expression and high level expression of heavy chain antibodies with variable regions encoded by human V, D, and J genes. Immunization of transgenic rats resulted in production of high titer serum responses of antigen-specific heavy chain antibodies. These transgenic rats expressing heavy chain antibodies with a human VDJ region were called UniRats™.

Example 2

Immunization

DNA Immunization with CD19.

Six UniRat animals were immunized according to a standard DNA-based immunization protocol using an expression vector that contains the CD19 sequence. After an immunization time course of 45 days, serum was collected from rats to determine serum titers.

Example 3

Binding to CD19-Expressing Cell Lines

FIG. 4 summarizes target binding activity of anti-CD19 heavy-chain antibodies (HCAb) described. Column 1 indicates the clone ID of the HCAb. Column 2 indicates binding to Raji cells measured as fold over background MFI signal. Column 3 indicates binding to Ramos cells measured as fold over background MFI signal. Column 4 indicates binding to CHO cells stably expressing human CD19 measured as fold over background MFI signal. Column 5 indicates binding to CHO cells that do not express CD19 protein measured as fold over background MFI signal.

Example 4

Bispecific Antibody Mediated Killing of Daudi Human Tumor Cells Through Redirection of Activated T Cells A CD19-positive tumor cell line was dye-labeled and incubated with increasing amounts of bispecific antibody in the presence of pre-activated human T cells. The bispecific antibody was composed of an anti-CD3 binding arm paired with the anti-CD19 VH binding domain indicated in FIG. 5B (clone ID: 334354). Two CD22×CD3 bispecific antibodies in the same format were included as positive controls. The negative control antibody includes a VH binding domain that does not bind to CD19. CD22-negative K562 cells exhibited no specific lysis (data not shown).

Example 5

CD19 Protein Binding

Figure 6:
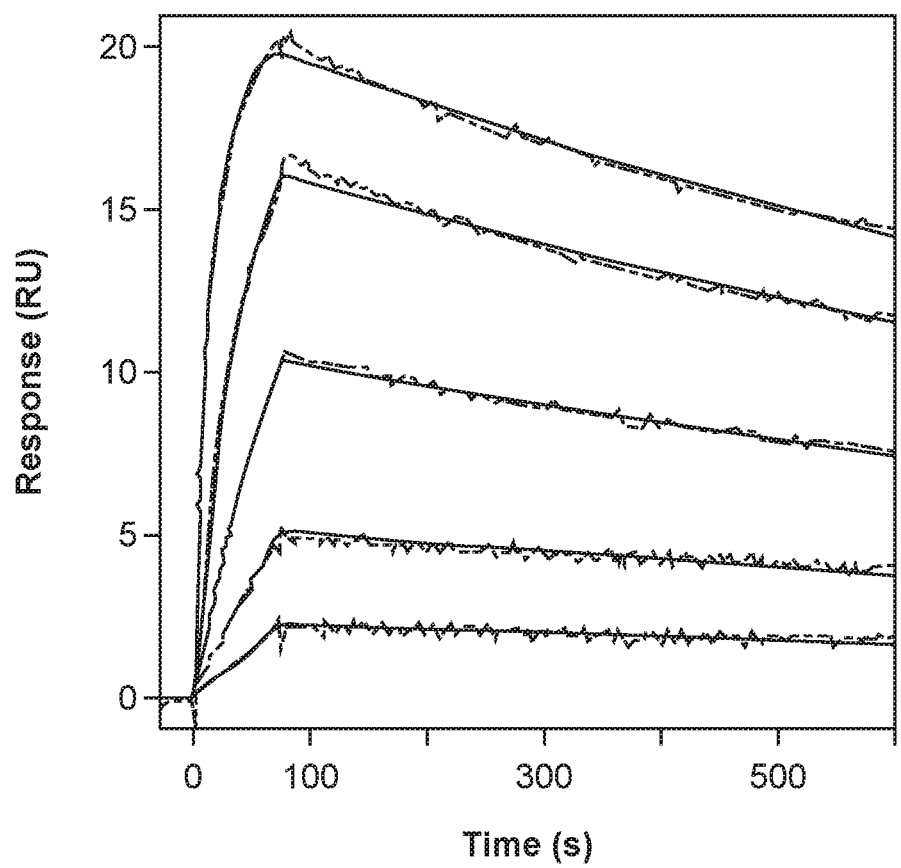
FIG. 6 is a graph showing protein binding response as a function of time.

Kinetics experiments to determine the antigen and antibody affinities were performed on a
Biacore T100 instrument. Penta Anti-His mAB was coupled to CM7 biosensors chip using standard amine coupling. Acro CD19 (20-291) His tagged (lot C52P2-7C1F1-GJ) was dissolved in 200 ul of water then diluted 1/100 and captured on the anti-His mAb chip. Clone ID#334354 was tested at 3.6 uM as the highest concentration in a 3 fold dilution series. Data was fit to a 1:1 interaction model as shown in FIG. 6.

Example 6

Tumor Models

Description of procedures: NOG mice were engrafted intravenously with luciferase-labeled human tumor cells. Human PBMCs were injected 5 days post tumor engraftment, and on day 6 the antibodies were administered. Mice were treated by injecting intravenously anti-CD19×CD3 antibodies and negative control (NC) four times per week at 10 ug per dose. Tumor burden was assessed every 2-4 days for up to 1 month.

Choice of Animal and Species: The experiments were conducted in NOG mice transplanted with 15 million human PBMCs.

Figure 7:
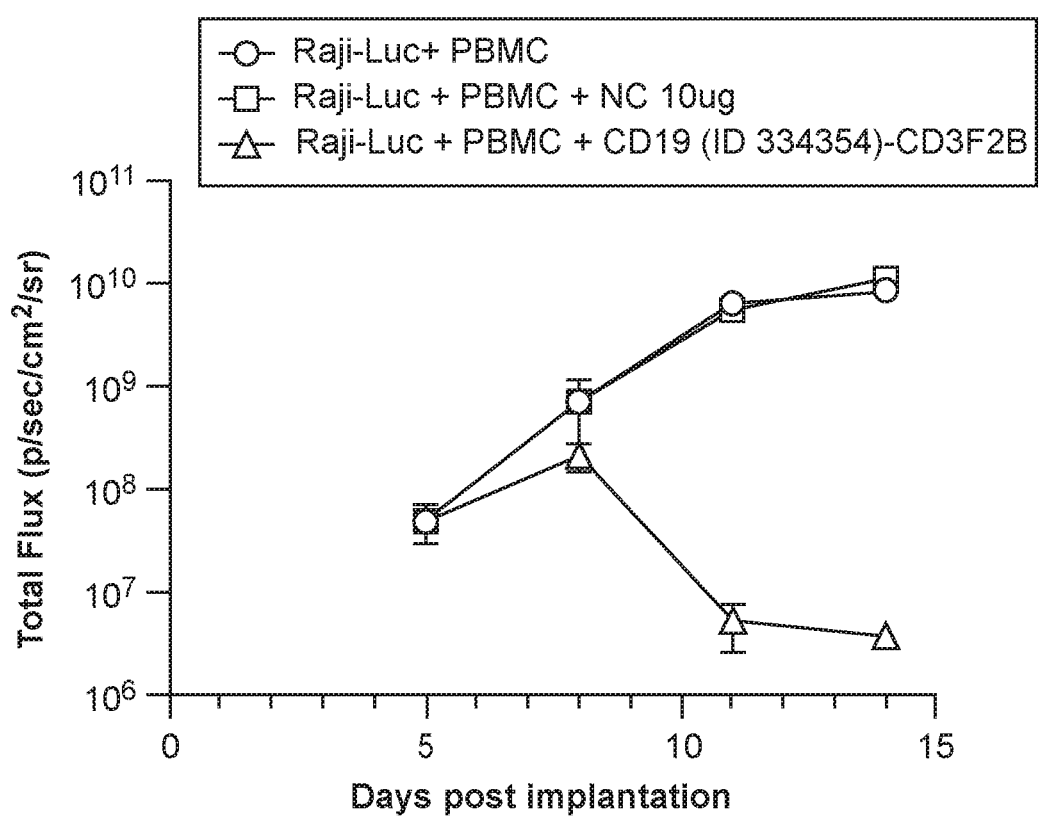
FIG. 7 is a graph showing tumor burden as a function of time (days post implantation) for a tumor model experiment.

Sample sizes: 5 or more animals per group were exposed to tumors and treated with anti-CD19×CD3 or control antibodies. In general, past biochemical and physiological studies indicated that a sample size of n=4-6 animals provides adequate statistical power (i.e., 80% power) to detect an effect size of 1.6 SD units between treatment conditions using a two-sample t-test with a 0.05 two-sided significance level. Anti-CD19×CD3 antibodies statistically significantly reduced tumor growth in animal models, as demonstrated by the data in FIG. 7.

Example 7

In Vitro Cytotoxicity Model

Figure 8:
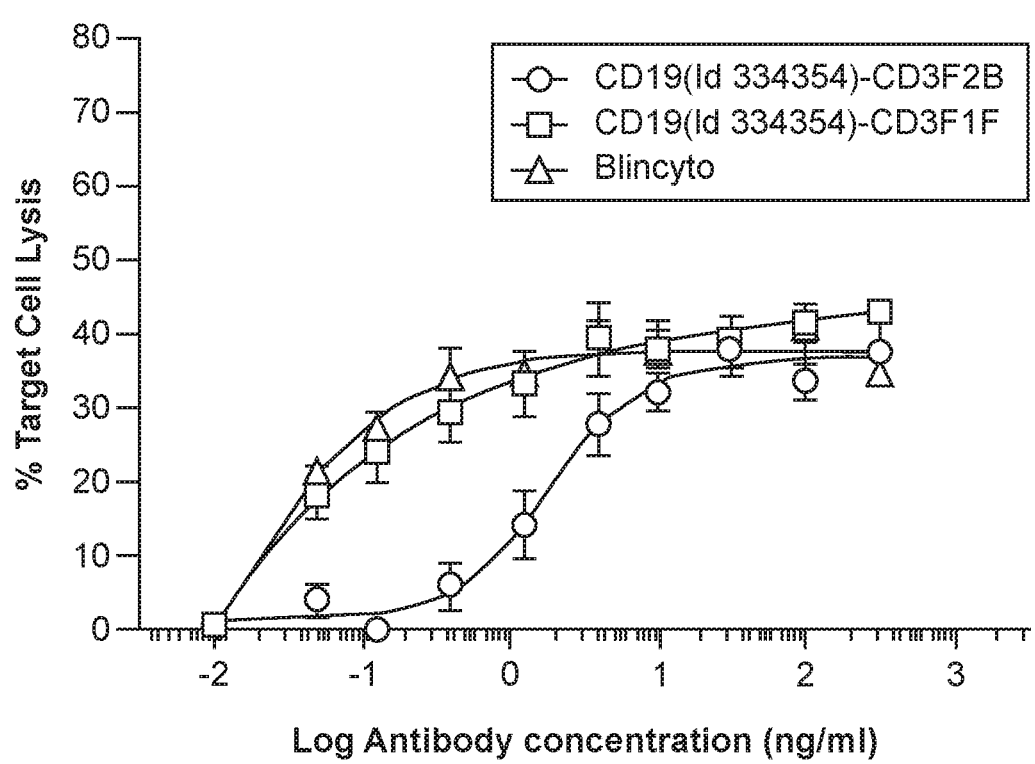
FIG. 8 is a graph showing target cell lysis (cytotoxicity) as a function of antibody concentration.

A CD19-positive (CD19+) tumor cell line was labelled with dye and incubated with increasing amounts of bispecific antibody (CD19×CD3) in the presence of pre-activated T cells. Post incubation for 6 hours, the fluorescence from release of the dye was analyzed. The bispecific antibody was composed of an anti-CD3 binding arm (Family F2B) paired with the anti-CD19 VH binding (334354) domain, as depicted schematically in FIG. 5B. Two other bispecific antibodies were included, a) anti-CD3 binding arm (Family F1F) paired with anti-CD19 VH binding domain (334354) and b) Blincyto. The results are provided in FIG. 8, and demonstrate that the percentage of target cell lysis increased in a concentration-dependent manner for all of the bispecific antibodies that were tested. The percentage of target cell lysis increased at a faster rate, as a function of antibody concentration, for the CD19(Id334354)×CD3F2B and CD19 (Id334354)×CD3F1F, as compared to Blincyto. Maximum lysis was the same between CD19(Id334354)×CD3F2B, CD19(Id334354)×CD3F1F, and Blincyto.

Example 8

In Vitro Cytokine Model

Figure 9:
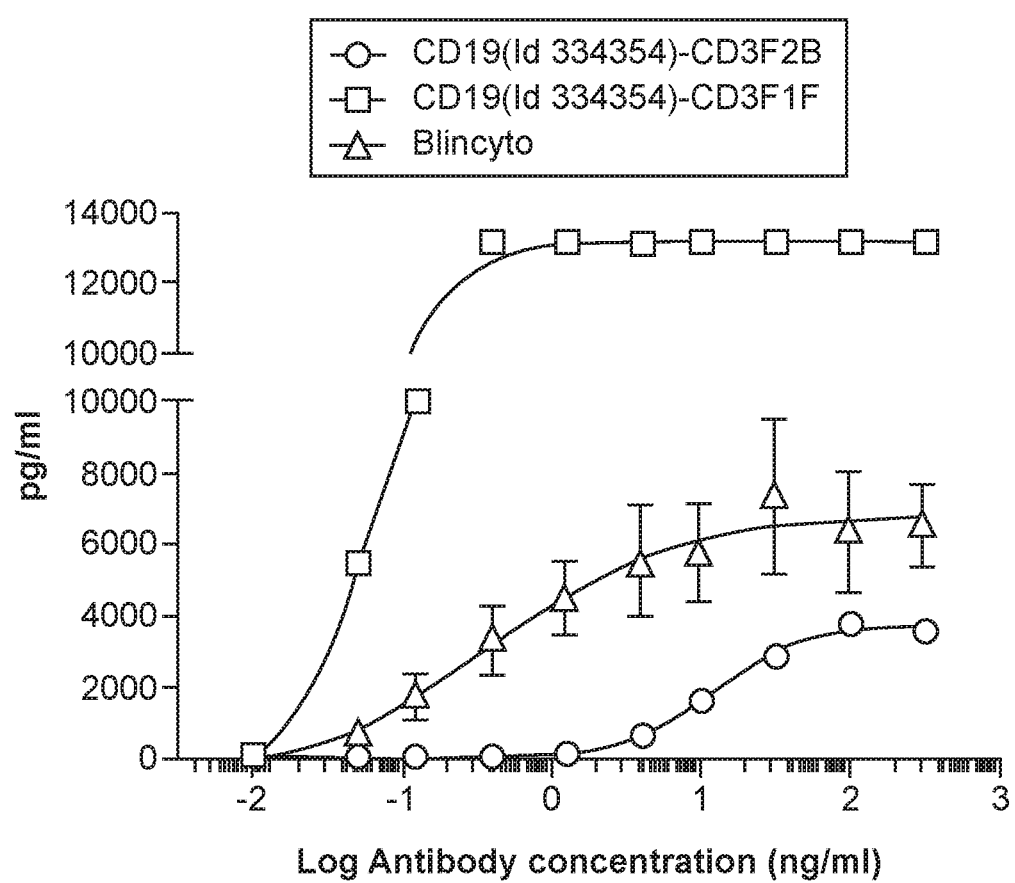
FIG. 9 is a graph showing concentration of released cytokines as a function of antibody concentration.

A CD19-positive (CD19+) tumor cell line was incubated with increasing amounts of bispecific antibody (CD19× CD3) in the presence of resting T cells for 24. Post incubation supernatants were harvested and measured for cytokines. The bispecific antibody was composed of an anti-CD3 binding arm (Family F2B) paired with the anti-CD19 VH binding (334354) domain, as depicted schematically in FIG. 5B. Two other bispecific antibodies were included, a) anti-CD3 binding arm (Family F1F) paired with anti-CD19 VH binding domain (334354) and b) Blincyto. The results are provided in FIG. 9, and demonstrate that the amount of cytokine release varied for each antibody, and increased in a concentration-dependent manner Specifically, the CD19 (Id 334354)×CD3F2B bispecific antibody showed the lowest level of cytokine release. Blincyto demonstrated higher cytokine release as a function of antibody concentration, and the CD19(Id 334354)×CD3F1F bispecific antibody showed the highest levels of cytokine release. Maximum cytokine production was the highest for CD19(Id334354)×CD3F1F followed by Blincyto, and lowest for CD19(Id334354)× CD3F2B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A heavy chain-only antibody that binds to CD19, wherein the heavy chain-only antibody comprises a heavy chain variable region comprising the CDR1 sequence set forth in SEQ ID NO: 4, the CDR2 sequence set forth in SEQ ID NO: 10, and the CDR3 sequence set forth in SEQ ID NO: 13.

2. The heavy chain-only antibody of claim 1, wherein said CDR1, CDR2, and CDR3 sequences are present in a human framework.

3. The heavy chain-only antibody of claim 1, further comprising a heavy chain constant region sequence in the absence of a CH1 sequence.

4. The heavy chain-only antibody of claim 1, comprising a heavy chain variable region having at least 95% sequence identity to SEQ ID NO: 17.

5. The heavy chain-only antibody of claim 1, comprising a heavy chain variable region comprising SEQ ID NO: 17.

6. A heavy chain-only antibody that binds to CD19, wherein the heavy chain-only antibody comprises a heavy chain variable region comprising the CDR1 sequence set forth in SEQ ID NO: 4, the CDR2 sequence set forth in SEQ ID NO: 10, and the CDR3 sequence set forth in SEQ ID NO: 13, in a human VH framework.

7. A multi-specific antibody comprising the heavy chain-only antibody of claim 1.

8. The multi-specific antibody of claim 7, which is bispecific.

9. The multi-specific antibody of claim 7, having binding affinity to an effector cell.

10. The multi-specific antibody of claim 7, having binding affinity to a T-cell antigen.

11. The multi-specific antibody of claim 10, having binding affinity to CD3.

12. The heavy chain-only antibody of claim 1, which is in a CAR-T format.

13. A pharmaceutical composition comprising the heavy chain-only antibody of claim 1.

14. A method for the treatment of a B-cell disorder characterized by expression of CD19, comprising administering to a subject the antibody of claim 1.

15. A kit for treating a B-cell disorder characterized by expression of CD19 in an individual in need, the kit comprising the antibody of claim 1, and instructions for use.

16. The kit of claim 15, further comprising at least one additional reagent.

17. The kit of claim 16, wherein the at least one additional reagent comprises a chemotherapeutic drug.

18. A multi-specific antibody comprising an antigen-binding domain that binds to CD19, wherein the antigen binding domain comprises a heavy chain variable region comprising the CDR1 sequence set forth in SEQ ID NO: 4, the CDR2 sequence set forth in SEQ ID NO: 10, and the CDR3 sequence set forth in SEQ ID NO: 13.

19. The multi-specific antibody of claim 18, comprising a heavy chain variable region comprising SEQ ID NO: 17.

20. The multi-specific antibody of claim 18, which is bispecific.

21. The multi-specific antibody of claim 18, having binding affinity to CD3.

22. A pharmaceutical composition comprising the multi-specific antibody of claim 18.

23. A method for the treatment of a B-cell disorder characterized by expression of CD19, comprising administering to a subject the multi-specific antibody of claim 18.

24. A bispecific antibody comprising: a) a heavy chain/light chain pair that has binding specificity for CD3, and b) a heavy chain comprising an antigen-binding domain that has binding specificity for CD19, wherein said antigen binding domain comprises a heavy chain variable region comprising the CDR1 sequence set forth in SEQ ID NO: 4, the CDR2 sequence set forth in SEQ ID NO: 10, and the CDR3 sequence set forth in SEQ ID NO: 13.

25. The bispecific antibody of claim 24, comprising a heavy chain variable region comprising SEQ ID NO: 17.

26. An antibody that binds specifically to CD19, wherein the antibody comprises a heavy chain variable domain comprising the CDR1 sequence set forth in SEQ ID NO: 4, the CDR2 sequence set forth in SEQ ID NO: 10, and the CDR3 sequence set forth in SEQ ID NO: 13, in a human VH framework.

27. The antibody of claim 26, comprising a heavy chain variable region comprising SEQ ID NO: 17.

28. The method of claim 14, wherein the disorder is diffuse large B-cell lymphoma (DLBCL).

29. The method of claim 14, wherein the disorder is acute lymphoblastic leukemia (ALL).

30. The method of claim 14, wherein the disorder is non-Hodgkin's lymphoma (NHL).

31. The method of claim 23, wherein the disorder is diffuse large B-cell lymphoma (DLBCL).

32. The method of claim 23, wherein the disorder is acute lymphoblastic leukemia (ALL).

33. The method of claim 23, wherein the disorder is non-Hodgkin's lymphoma (NHL).

34. A polynucleotide encoding the antibody of claim 1.

35. A polynucleotide encoding the multi-specific antibody of claim 18.

36. A vector comprising the polynucleotide of claim 34.

37. A vector comprising the polynucleotide of claim 35.

38. A cell comprising the vector of claim 36.

39. A cell comprising the vector of claim 37.

\* \* \* \* \*

```
                           SEQUENCE LISTING

<160> NUMBER OF SEQ ID NOS: 30

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Asn Tyr Trp
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Phe Thr Phe Ser Ser Phe Trp
1               5

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Phe Thr Phe Ser Ser Tyr Trp
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Ser Phe Ser Asp Phe Trp
1               5

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 5

Gly Phe Thr Phe Ser Asp Tyr Trp
1               5

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Phe Thr Phe Ser Asp Tyr Tyr
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ile Asn Gln Asp Gly Ser Asp Lys
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Met Asn Gln Asp Gly Ser Glu Lys
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Asn Gln Asp Gly Ser Glu Lys
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 10

Ile Ser Gln Ala Gly Ser Glu Lys
1               5

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Lys Gln Asp Gly Ser Glu Lys
1               5

<210> SEQ ID NO 12
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ile Asn Lys Ala Gly Ser Glu Glu
1               5

<210> SEQ ID NO 13
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ala Ser Gly Val Tyr Ser Phe Asp Tyr
1               5

<210> SEQ ID NO 14
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Gln Glu Trp Val
        35                  40                  45

Ala Thr Ile Asn Gln Asp Gly Ser Asp Lys Asp Tyr Val Asp Ser Val
    50                  55                  60

Lys Gly Arg Phe Thr Ile Ser Arg Asp Asn Ala Lys Ser Leu Tyr
65                  70                  75                  80
```

```
Leu Gln Met Asn Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser
        115

<210> SEQ ID NO 15
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Thr Phe Ser Ser Phe
            20                  25                  30

Trp Met Ser Trp Val Arg Gln Ala Pro Gly Lys Gly Leu Glu Trp Val
        35                  40                  45

Ala Thr Met Asn Gln Asp Gly Ser Glu Lys Asp Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Thr Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser
        115

<210> SEQ ID NO 16
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Val Glu Ser Gly Gly Gly Met Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Thr Ile Asn Gln Asp Gly Ser Glu Lys Asp Tyr Val Asp Ser Val
    50                  55                  60

Lys Gly Arg Phe Thr Ile Ser Arg Asp Asn Ala Lys Lys Ser Leu Leu
65                  70                  75                  80

Leu Gln Met Asn Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110
```

Thr Val Ser Ser
        115

<210> SEQ ID NO 17
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Trp Met Ser Trp Val Arg Gln Ala Pro Gly Lys Gly Leu Glu Trp Val
        35                  40                  45

Ala Thr Ile Ser Gln Ala Gly Ser Glu Lys Asp Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala His Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser
        115

<210> SEQ ID NO 19
<211> LENGTH: 116
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19
```

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Asn Ile Asn Lys Ala Gly Ser Glu Glu Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser
            115

```
<210> SEQ ID NO 20
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20
```

Glu Val Gln Leu Val Glu Ser Gly Gly Gly Leu Val Gln Pro Gly Gly
1               5                   10                  15

Ser Leu Thr Leu Ser Cys Val Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Pro Lys Asn Ser Leu Tyr
65                  70                  75                  80

Leu Gln Met Asp Ser Leu Arg Val Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser
            115

```
<210> SEQ ID NO 21
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Glu Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser
        115

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (6)..(6)
<223> OTHER INFORMATION: /replace="Asn"
<220> FEATURE:
<221> NAME/KEY: VARIANT
<222> LOCATION: (7)..(7)
<223> OTHER INFORMATION: /replace="Phe"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 22

Gly Phe Thr Phe Ser Ser Tyr Trp
1               5

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Met"
<220> FEATURE:
<221> NAME/KEY: VARIANT
<222> LOCATION: (2)..(2)
<223> OTHER INFORMATION: /replace="Ser" or "Lys"
<220> FEATURE:
<221> NAME/KEY: VARIANT

```
<222> LOCATION: (3)..(3)
<223> OTHER INFORMATION: /replace="Lys"
<220> FEATURE:
<221> NAME/KEY: VARIANT
<222> LOCATION: (4)..(4)
<223> OTHER INFORMATION: /replace="Ala"
<220> FEATURE:
<221> NAME/KEY: VARIANT
<222> LOCATION: (7)..(7)
<223> OTHER INFORMATION: /replace="Glu"
<220> FEATURE:
<221> NAME/KEY: VARIANT
<222> LOCATION: (8)..(8)
<223> OTHER INFORMATION: /replace="Glu"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 23

Ile Asn Gln Asp Gly Ser Asp Lys
1               5

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Gly Gly Gly Ser
1               5

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Gly Gly Gly Ser Gly Gly Gly Gly Ser
1               5                   10

<210> SEQ ID NO 26
<211> LENGTH: 330
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 327
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 28
<211> LENGTH: 330
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 29
<211> LENGTH: 327
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Ala Ala Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 30
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: /note="This sequence may encompass 1-10 'Gly
      Gly Gly Gly Ser' repeating units"

<400> SEQUENCE: 30

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
50
```